US 6,736,791 B1

(12) United States Patent
Tu et al.

(10) Patent No.: US 6,736,791 B1
(45) Date of Patent: May 18, 2004

(54) GLAUCOMA TREATMENT DEVICE

(75) Inventors: Hosheng Tu, Tustin, CA (US); Olav G. Bergheim, Laguna Hills, CA (US); Morteza Gharib, San Marino, CA (US)

(73) Assignee: Glaukos Corporation, Laguna Hills, CA (US)

( * ) Notice: Subject to any disclaimer, the term of this patent is extended or adjusted under 35 U.S.C. 154(b) by 268 days.

(21) Appl. No.: 09/704,276

(22) Filed: Nov. 1, 2000

Related U.S. Application Data

(63) Continuation-in-part of application No. 09/549,350, filed on Apr. 14, 2000.

(51) Int. Cl.$^7$ ................................................ A61M 5/00
(52) U.S. Cl. ............................ 604/8; 604/28; 128/898
(58) Field of Search .................... 604/8–10, 19, 604/27, 28, 30, 48, 264, 541, 93.01, 94.01; 128/898; 600/561, 573, 579; 606/6, 100, 108

(56) References Cited

U.S. PATENT DOCUMENTS

| | | |
|---|---|---|
| 3,788,327 A | 1/1974 | Donowitz et al. |
| 4,037,604 A | 7/1977 | Newkirk |
| 4,168,697 A | 9/1979 | Cantekin |
| 4,175,563 A | 11/1979 | Arenberg et al. |
| 4,402,681 A | 9/1983 | Haas et al. |
| 4,428,746 A | 1/1984 | Mendez |
| 4,521,210 A | 6/1985 | Wong |
| 4,554,918 A | 11/1985 | White |
| 4,604,087 A | 8/1986 | Joseph |
| 4,634,418 A | 1/1987 | Binder |
| 4,722,724 A | 2/1988 | Schocket |
| 4,750,901 A | 6/1988 | Molteno |
| 4,846,172 A | 7/1989 | Berlin |
| 4,886,488 A | 12/1989 | White |
| 4,936,825 A | 6/1990 | Ungerleider |

(List continued on next page.)

FOREIGN PATENT DOCUMENTS

| | | |
|---|---|---|
| AU | 2000072059 A1 | 12/2000 |
| EP | 1 114 627 A1 | 11/2000 |
| WO | WO 89/00869 | 2/1989 |
| WO | WO 92/19294 | 11/1992 |
| WO | WO 94/13234 | 6/1994 |
| WO | WO 98/30181 | 1/1998 |
| WO | WO 00/64389 | 4/2000 |
| WO | WO 00/64390 | 4/2000 |
| WO | WO 00/64391 | 4/2000 |
| WO | WO 00/72788 A1 | 12/2000 |
| WO | WO 01/78631 | 10/2001 |
| WO | WO 01/78656 A2 | 10/2001 |
| WO | WO 03/015659 A2 | 2/2003 |

OTHER PUBLICATIONS

Phillip C. Jacobi, MD, Thomas S. Dietlein, MD. and Gunter K. Krieglstein, MD., Goniocurettage for Removing Trabecular Meshwork: Clinical Results of a New Surgical Technique in Advanced Cronic Open–Angle Glaucoma, *American Journal of Ophthalmology*, May 1999, pp. 505–510.

Phillip C. Jacobi, MD, Thomas S. Dietlein, MD. and Gunter K. Krieglstein, MD., Bimanual Trabecular Aspiration in Pseudoexfoliation Glaucoma, *Ophthalmology*, 1998, vol. 105, No. 5, May 1998, pp. 886–894.

(List continued on next page.)

*Primary Examiner*—Glenn K. Dawson
*Assistant Examiner*—Jennifer Maynard
(74) *Attorney, Agent, or Firm*—Knobbe Martens Olson & Bear, LLP.

(57) ABSTRACT

A glaucoma treatment device for directing the flow of aqueous humor and bypassing trabecular meshwork is disclosed. The device comprises an inlet section, an outlet section, a middle section, and at least one lumen for transmitting aqueous humor within the glaucoma device. The lumen extends through at least one of the sections, and the outlet section is substantially perpendicular to the middle section, and fits within a conduit of aqueous humor outflow in the eye.

2 Claims, 10 Drawing Sheets

U.S. PATENT DOCUMENTS

| | | | |
|---|---|---|---|
| 4,946,436 | A | 8/1990 | Smith |
| 4,968,296 | A | 11/1990 | Ritch et al. |
| 5,041,081 | A | 8/1991 | Odrich |
| 5,092,837 | A | 3/1992 | Ritch et al. |
| 5,095,887 | A | 3/1992 | Leon et al. |
| 5,127,901 | A * | 7/1992 | Odrich .................... 604/9 |
| 5,129,895 | A | 7/1992 | Vassiliadis et al. |
| 5,171,213 | A | 12/1992 | Price, Jr. |
| 5,178,604 | A | 1/1993 | Baerveldt et al. |
| 5,180,362 | A | 1/1993 | Worst |
| 5,300,020 | A | 4/1994 | L'Esperance, Jr. |
| 5,338,291 | A | 8/1994 | Speckman et al. |
| 5,346,464 | A | 9/1994 | Camras |
| 5,360,399 | A | 11/1994 | Stegmann |
| 5,370,607 | A | 12/1994 | Memmem |
| 5,372,577 | A | 12/1994 | Ungerleider |
| 5,397,300 | A | 3/1995 | Baerveldt et al. |
| 5,433,701 | A | 7/1995 | Rubinstein |
| 5,454,796 | A | 10/1995 | Krupin |
| 5,472,440 | A | 12/1995 | Beckman |
| 5,476,445 | A | 12/1995 | Baerveldt et al. |
| 5,486,165 | A | 1/1996 | Stegmann |
| 5,520,631 | A | 5/1996 | Nordquist et al. |
| 557,453 | A | 9/1996 | Schalz et al. |
| 5,558,629 | A | 9/1996 | Baerveldt et al. |
| 5,558,630 | A | 9/1996 | Fisher |
| RE35,390 | E | 12/1996 | Smith |
| 5,601,094 | A | 2/1997 | Reiss |
| 5,601,549 | A | 2/1997 | Miyagi |
| 5,626,558 | A * | 5/1997 | Suson .................... 604/8 |
| 5,626,559 | A | 5/1997 | Solomon |
| 5,651,783 | A | 7/1997 | Reynard |
| 5,676,679 | A | 10/1997 | Simon et al. |
| 5,704,907 | A | 1/1998 | Nordquist et al. |
| 5,743,868 | A | 4/1998 | Brown et al. |
| 5,752,928 | A | 5/1998 | de Roulhac et al. |
| 5,807,302 | A | 9/1998 | Wandel |
| 5,830,139 | A | 11/1998 | Abreu |
| 5,836,939 | A | 11/1998 | Negus et al. |
| 5,865,831 | A | 2/1999 | Cozean et al. |
| 5,868,697 | A | 2/1999 | Richter et al. |
| 5,879,319 | A * | 3/1999 | Pynson et al. .................. 604/8 |
| 5,882,327 | A | 3/1999 | Jacob |
| 5,886,822 | A | 3/1999 | Spitzer |
| 5,893,837 | A | 4/1999 | Eagles et al. |
| 5,968,058 | A | 10/1999 | Richter et al. |
| 5,981,598 | A | 11/1999 | Tatton |
| 6,004,302 | A | 12/1999 | Brierley |
| 6,007,510 | A * | 12/1999 | Nigam .................... 604/8 |
| 6,007,511 | A | 12/1999 | Prywes |
| 6,050,970 | A | 4/2000 | Baervelt |
| 6,059,772 | A | 5/2000 | Hsia et al. |
| 6,228,873 | B1 | 5/2001 | Brandt et al. |
| 6,266,182 | B1 | 7/2001 | Morita |
| 6,268,398 | B1 | 7/2001 | Ghosh et al. |
| 6,342,058 | B1 | 1/2002 | Portney |
| 6,375,642 | B1 | 4/2002 | Grieshaber et al. |
| 6,450,984 | B1 * | 9/2002 | Lynch et al. .................... 604/8 |
| 6,464,724 | B1 | 10/2002 | Lynch et al. |
| 6,533,768 | B1 | 3/2003 | Hill |
| 6,544,249 | B1 | 4/2003 | Yu et al. |

OTHER PUBLICATIONS

Phillip C. Jacobi, MD, Thomas S. Dietlein, MD. and Gunter K. Krieglstein, MD., Microendoscopic Trabecular Surgery in Glaucoma Management *Ophthalmology*, vol. 106, No. 3, pp. 538–544.

L. jay Katz, M.D., A Call for Innovative Operations for Glaucoma, *Arch Ophthalmology*, Mar. 2000, vol. 118, pp. 412–413.

Arthur L. Schwartz, MD, and Douglas R. Anderson, MD, Trabeculaar Surgery, *Arch Ophthalmol*, vol. 92, Aug. 1974, pp. 134–138.

R. A. Hill, Q. Ren, D. C. Nguyen, L–H. Liaw, and M. W. Berns, Free–electron Laser (FEL) Ablation of Ocular Tissues, *Laser Med Sci 1998*, pp. 13: 219–228.

Maurice H. Luntz, MD, and D. G. Livingston, B.SC., Trabeculotomy AB Externo and Trabeculectomy in Congenital and Adult–Onset Glaucoma, *American Journal of Ophthalmology*, Feb. 1977, vol. 83, No. 2, pp. 174–179.

W. M. Grant, MD, Further Studies on Facility of Flow Through the Trabecular Meshwork, *A.M.A. Archives of Ophthalmology*, Oct. 1958, vol. 60, pp. 523–533.

Richard A. Hill, MD, George Baerveldt, MD, Serdar A. Ozler, MD, Michael Pickford BA, Glen A. Profeta, BS, and Michael W Berns, PhD, Laser Trabecular Ablation (LTA), *Laser Surgery and Medicine*, 1991, vol. 11, pp. 341–346.

Detlev Spiegel, MD Karin Kobuch, MD, Richard A. Hill, MD., Ronald L. Gross, MD., Schlemm's Canal Implant: A New Method to Lower Intraocular Pressure in patients With POAG?, *Ophthalmic Surgery and Lasers*, Jun. 1999, vol. 30, No. 6, pp. 492–494.

Anselm Kampik and Franz Grehn, Nutzen und Risiken augenärztlicher Therapie, *Hauptreferate der XXXIII. Essener Fortbildung für Augenärzte*, Dec. 1998. (English translated version enclosed Benefits and Risks of Ophthalmological Therapy).

Detlev Spiegel, 7 *Chirurgische Glaukomtherapie*, pp. 79–88.

PCT Publication—WO 01/50943, International Publication Date Jul. 19, 2001.

U.S. Patent Publication No. US 2002/0026200; publication date Feb. 28, 2002; Inventor: Savage; Title: Method and Apparatus for Treatment of Glaucoma.

U.S. Patent Publication No. US 2002/0072673 A1; publication date Jun. 13, 2002; Inventor Yamamoto et al; Title: Treatment of Ocular Disease.

U.S. patent publication No. US 2003/0069637 A1; publication date Apr. 10, 2003; Inventor: Lynch, et al. Title: Stent Device and Method for Treating Glaucoma.

Hans Hoerauf, Christopher Wirbelauer, Christian Scholz, Ralf Engelhardt, Peter Koch, Horst Laqua, and Reginald Birngruber, *Slit–Lamp–Adapted Optical Coherence Tomography of the Anterior Segment*, Graefe's Arch Clin. Exp. Ophthalmol, May, 1999, vol. 238, pp. 8–18.

Sumita Radhakrishnam, Andrew M. Rollins, Jonathan E. Roth, S. Yazdanfar, Volker Westphal, David Bardenstein & Joseph Izatt, *Real–time Optical Coherence Tomography of the Anterior Segment at 1310 NM*, Arch Opthalmology, Aug. 2001, vol. 119, pp. 1179–1185.

I. Grierson, R. C. Howes & Q. Wang, *Age–related Changes in the Canal of Schlemm*, Exp. Eye Res., 1985, vol. 39, pp. 505–512.

Luanna K. Putney, Cecile Rose T. Vibat, & Martha E. O'Donnell, *Intracellular C1 Regulates Na–K–C1 Cotransport Activity in Human Trabecular Meshwork Cells*, 1999 American Physiological Society, Sep. 1999, pp. C–373 through C–383.

Edited by Kevin Strange, *Cellular and Molecular Physiology of Cell Volume Regulation*, Library of Congress Cataloging in–Publication Data, CRC Press, Inc., pp. 312–321.

William Tatton, Ruth M.E. Chalmers–Redman, Ajay Sud, Steven M. Podos, & Thomas Mittag, *Maintaining Mitochrondrial Membrane Impermeability: An Opportunity for New Therapy in Glaucoma?*, Survey of Opthalmology, vol. 45, Supplement 3, May 2001, pp. S–277 through S–283.

Robert W. Nickells, *Apoptosis of Retinal Ganglion Cells in Glaucoma: An Update of the Molecular Pathways Involved in Cell Death*, Survey of Opthalmology, vol. 43, Supplement 1, Jun. 1999, pp. S–151 through S–161.

Grune & Stratton, Harcourt Brace Jovanovich Publishers, edited by J.E. Cairns, Glaucoma, vol. 1, Chapter 14, *Anatomy of the Acqueous Outflow Channels*, by Johannes W. Rohen, pp. 277–296.

Yasuhiro Matsumoto & Douglas H. Johnson, *Trabecular Meshwork Phagocytosis in Glaucomatous Eyes*, Ophthalmologica 1977, vol. 211, pp. 147–152.

M. Bruce Shields, M.D., A Study Guide for Glaucoma,; Aqueous Humor Dynamics, Copyright 1982, pp. 6–43.

M. A. Johnstone, R. Stegmann & B.A. Smit, American Glaucoma Society, 12th Annual Meeting, *Cylindrical Tubular Structures Spanning from Trabecular Meshwork Across SC*: Laboratory Studies with SEM, TEM & Tracers Correlated wwith Clinical Findings., p. 39.

W. G. Tatton, *Apoptotic Mechanisms in Neurodegeneration: Possible Relevance to Glaucoma*, European Journal of Ophthalmology 1999, Jan–Mar., vol. 9, Supplement 1, pp. S–22 through S29.

* cited by examiner

GLAUCOMA TREATMENT DEVICE

CROSS-REFERENCE TO RELATED APPLICATION

This application is a continuation-in-part of U.S. patent application Ser. No. 9/549,350, filed Apr. 14, 2000, and entitled "Apparatus and Method for Treating Glaucoma," the entire contents of which are incorporated herein by reference.

BACKGROUND OF THE INVENTION

The present invention generally relates to medical devices and methods for reducing intraocular pressure in the animal eye. More particularly, the present invention relates to the treatment of glaucoma by permitting aqueous humor to flow out of the anterior chamber through a surgically implanted pathway.

The human eye is a specialized sensory organ capable of light reception and able to receive visual images. The trabecular meshwork serves as a drainage channel and is located in anterior chamber angle formed between the iris and the cornea. The trabecular meshwork maintains a balanced pressure in the anterior chamber of the eye by draining aqueous humor from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is a constant flow of aqueous humor from the ciliary body to the eye's front chamber. The eye's pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

All current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10–15%); infection (a life long risk of 2–5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy

Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Trabeculopuncture

Q-switched Neodymiun (Nd) YAG lasers also have been investigated as an optically invasive technique for creating full-thickness holes in trabecular meshwork. However, the relatively small hole created by this trabeculopuncture technique exhibits a filling-in effect and fails.

Goniophotoablation/Laser Trabecular Ablation

Goniophotoablation is disclosed by Berlin in U.S. Pat. No. 4,846,172 and involves the use of an excimer laser to treat glaucoma by ablating the trabecular meshwork. This was demonstrated not to succeed by clinical trial. Hill et al. used an Erbium:YAG laser to create full-thickness holes through trabecular meshwork (Hill et al., Lasers in Surgery and Medicine 11:341–346, 1991). This technique was investigated in a primate model and a limited human clinical trial at the University of California, Irvine. Although morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage

This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanulostomy (VC) and non-penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous humor is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous humor through the surgical opening will continue. The risk of placing a glaucoma drainage device also includes hemorrhage, infection, and diplopia (double vision).

Examples of implantable shunts and surgical methods for maintaining an opening for the release of aqueous humor from the anterior chamber of the eye to the sclera or space beneath the conjunctiva have been disclosed in, for example, U.S. Pat. No. 6,059,772 to Hsia et al., and U.S. Pat. No. 6,050,970 to Baerveldt.

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have inspired ophthalmic surgeons to find other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to boldly examine new surgical approaches that may provide better and safer care for patients with glaucoma.

Therefore, there is a great clinical need for the treatment of glaucoma by a method that is faster, safer, and less expensive than currently available modalities.

SUMMARY OF THE INVENTION

Glaucoma surgical morbidity would greatly decrease if one were to bypass the focal resistance to outflow of aqueous only at the point of resistance, and to utilize remaining, healthy aqueous outflow mechanisms. This is in part because episcleral aqueous humor exerts a backpressure that prevents intraocular pressure from going too low, and one could thereby avoid hypotony. Thus, such a surgery would virtually eliminate the risk of hypotony-related maculopathy and choroidal hemorrhage. Furthermore, visual recovery would be very rapid, and the risk of infection would be very small (a reduction from 2–5% to about 0.05%).

Techniques performed in accordance with the present invention may be referred to generally as "trabecular bypass surgery." Advantages of the present invention include lowering intraocular pressure in a manner which is simple, effective, disease site-specific, and can potentially be performed on an outpatient basis.

In accordance with one aspect of the invention, trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated device is placed within the hole, serving as a stent.

In some embodiments, the device may be positioned across trabecular meshwork alone, without extending into the eye wall or sclera. The inlet end of the device is exposed to the anterior chamber of the eye while the outlet end is positioned at the exterior surface of the trabecular meshwork. In another embodiment, the outlet end is positioned at the exterior surface of the trabecular meshwork and into the fluid collection channels of the existing outflow pathways. In still another embodiment, the outlet end is positioned in Schlemm's canal. In an alternative embodiment, the outlet end enters into fluid collection channels (e.g., aqueous collector channels) up to the level of the aqueous veins, with the device inserted in a retrograde or antegrade fashion.

In some embodiments, the device is made of biocompatible material, which is either hollow, to allow the flow of aqueous humor, or solid, porous material that imbibes aqueous humor. One or more materials for the device may be selected from the following material types: porous material, semi-rigid material, soft material, hydrophilic material, hydrophobic material, hydrogel, elastic material, biodegradable material, and the like.

One or more materials for the glaucoma device may be selected from the following: polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polyimide, polysilison, silicone, polyurethane, Nylon, polypropylene, hydroxyapetite, titanium, and precious metal (e.g., gold, silver, or platinum). Other suitable filter types and materials for the device may be used in accordance with the invention and will be apparent to those of skill in the art.

In accordance with a further aspect of the invention, the device is relatively soft and somewhat curved at its outlet section to fit into the existing outflow pathways, such as Schlemm's canal. The outlet section may be curved around a curve center, and the middle section may extend substantially along a plane that contains the curve center. All or a portion of the cross section of one or more lumens may be in an elliptical (e.g., oval) shape. Furthermore, the outlet section inside the outflow pathway may have an appropriate shape, e.g., with a protuberance or barb projecting from it, to stabilize the device in place without undue suturing.

One aspect of the invention includes a method of placing a glaucoma device into an opening through trabecular meshwork and into an outflow pathway for aqueous humor. This glaucoma device includes an inlet section, an outlet section, and a middle section between the inlet section and the outlet section. The glaucoma device also includes at least one lumen that extends within at least one of the three sections for transmitting aqueous humor, and the outlet section is substantially perpendicular to the middle section. The outlet section includes a first outlet end and a second outlet end. In this aspect of the invention, the method includes advancing the first outlet end of the outlet section through the opening into a first part of the outflow pathway, and advancing the second outlet end of the outlet section through the opening into a second part of the outflow pathway.

The outlet section is, in one embodiment, an elongated element having a first outlet end and a second outlet end, wherein the middle section is connected to the outlet section between the first outlet end and the second outlet end. Stabilization or retention of the device in the eye may be further strengthened by inserting the first outlet end into a first side of Schlemm's canal, then inserting the second outlet end into a second, opposite side of Schlemm's canal. The angle between the long axis of the inlet section and the long axis of the middle section is advantageously between about 20 degrees and about 150 degrees, and preferably between about 30 degrees and about 60 degrees. This angle adapts the device for positioning the inlet section inside the anterior chamber of an eye.

In one embodiment, the device of the invention may include a flow-restricting member for restricting at least one component in fluid. The flow-restricting member may be a filter comprising one or more filtration materials selected from the following: expanded polytetrafluoroethylene, cellulose, ceramic, glass, Nylon, plastic, fluorinated material, or the like. The flow-restricting member may advantageously be a filter selected from the following group of filter types: hydrophobic, hydrophilic, membrane, microporous, and non-woven. The flow-restricting member acts to limit or prevent the reflux of any undesired component or contaminant of blood, such as red blood cells or serum protein, from the aqueous veins into the anterior chamber. It is useful to restrict one or more of the following component or contaminants: platelets, red blood cells, white blood cells, viruses, bacteria, antigens, and toxins.

In an alternate embodiment, the method may further include inserting a guidewire into the first part of the outflow pathway, wherein the step of advancing the first outlet end of the outlet section includes advancing the glaucoma device along the guidewire.

Among the advantages of trabecular bypass surgery in accordance with the invention is its simplicity. The microsurgery may potentially be performed on an outpatient basis with rapid visual recovery and greatly decreased morbidity. There is a lower risk of infection and choroidal hemorrhage, and there is a faster recovery, than with previous techniques.

Further features and advantages of the present invention will become apparent to one of skill in the art in view of the Detailed Description that follows, when considered together with the attached drawings and claims.

DETAILED DESCRIPTION OF EXEMPLARY EMBODIMENTS

FIGS. 1 to 9 illustrate an apparatus for the treatment of glaucoma by trabecular bypass surgery in accordance with the present invention.

Figure 1:
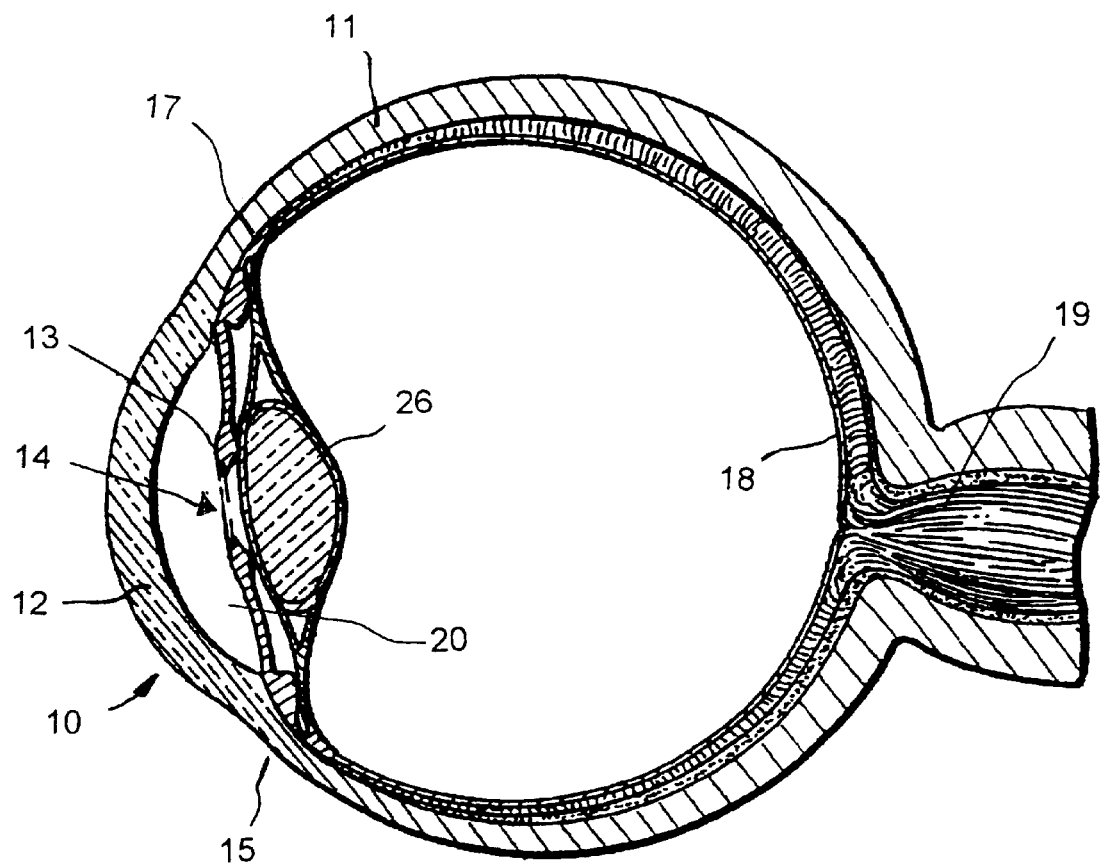
FIG. 1 is a sagittal sectional view of an eye.
Figure 2:
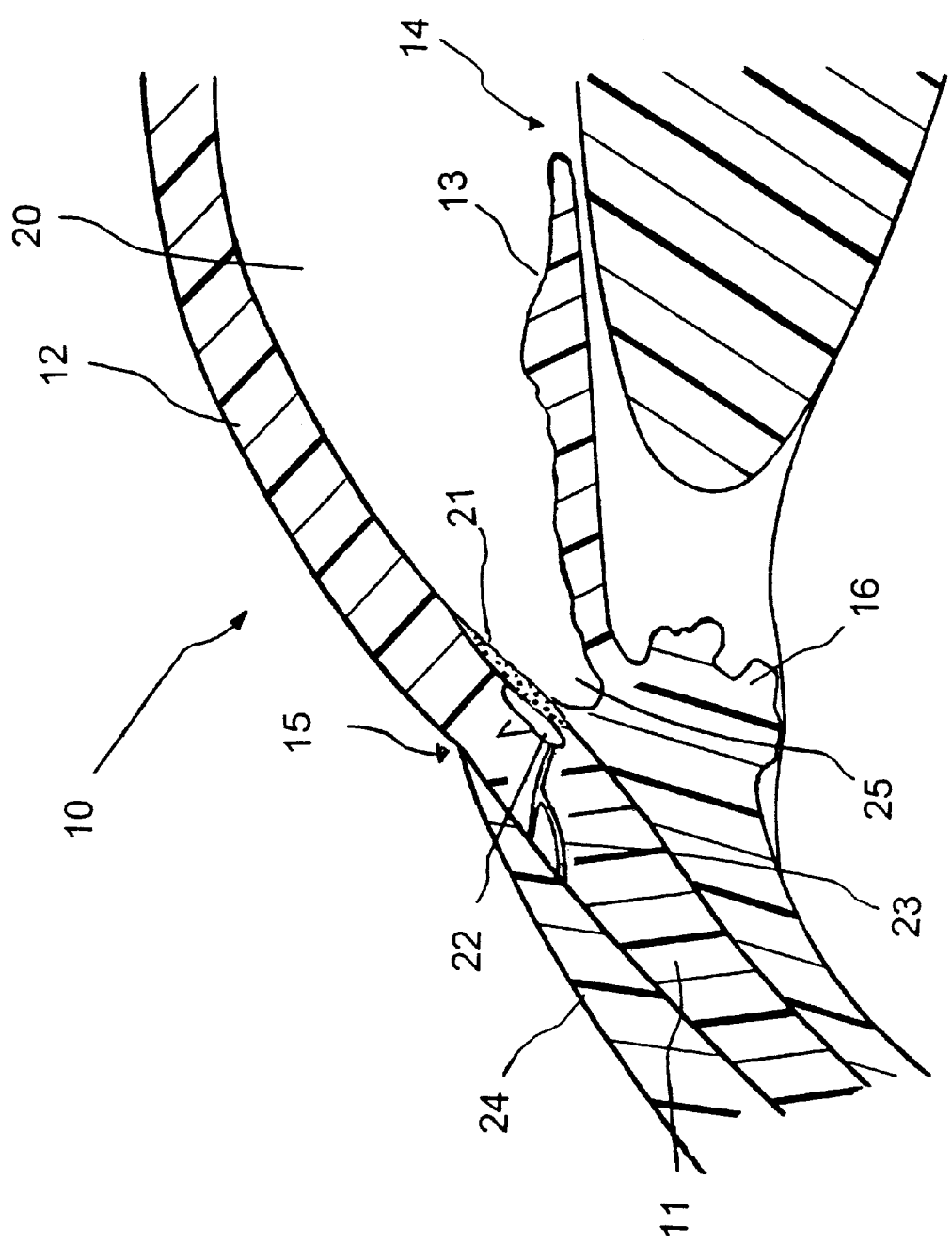
FIG. 2 is a cross-sectional view of the anterior chamber of an eye.

FIG. 1 is a sagittal sectional view of an eye 10, while FIG. 2 shows a close-up view, showing the relative anatomical locations of trabecular meshwork 21, the anterior chamber 20, and Schlemm's canal 22. Thick collagenous tissue known as sclera 11 covers the entire eye 10 except that portion covered by the cornea 12. The cornea 12 is a thin transparent tissue that focuses and transmits light into the eye and through the pupil 14, which is the circular hole in the center of the iris 13 (colored portion of the eye). The cornea 12 merges into the sclera 11 at a juncture referred to as the limbus 15. The ciliary body 16 extends along the interior of the sclera 11 and is coextensive with the choroid 17. The choroid 17 is a vascular layer of the eye 10, located between the sclera 11 and retina 18. The optic nerve 19 transmits visual information to the brain and is the anatomic structure that is progressively destroyed by glaucoma.

The anterior chamber 20 of the eye 10, which is bound anteriorly by the cornea 12 and posteriorly by the iris 13 and lens 26, is filled with aqueous humor ("aqueous"). Aqueous is produced primarily by the ciliary body 16, then moves anteriorly through the pupil 14 and reaches the anterior chamber angle 25, formed between the iris 13 and the cornea 12. In a normal eye, the aqueous is removed from the anterior chamber 20 through the trabecular meshwork 21. Aqueous passes through trabecular meshwork 21 into Schlemm's canal 22 and thereafter through the aqueous veins 23, which merge with blood-carrying veins and into systemic venous circulation. Intraocular pressure is maintained by the intricate balance between secretion and outflow of the aqueous in the manner described above. Glaucoma is, in most cases, characterized by the excessive buildup of aqueous humor in the anterior chamber 20, which leads to an increase in intraocular pressure. Fluids are relatively incompressible, and pressure is directed relatively equally throughout the eye.

Figure 8:
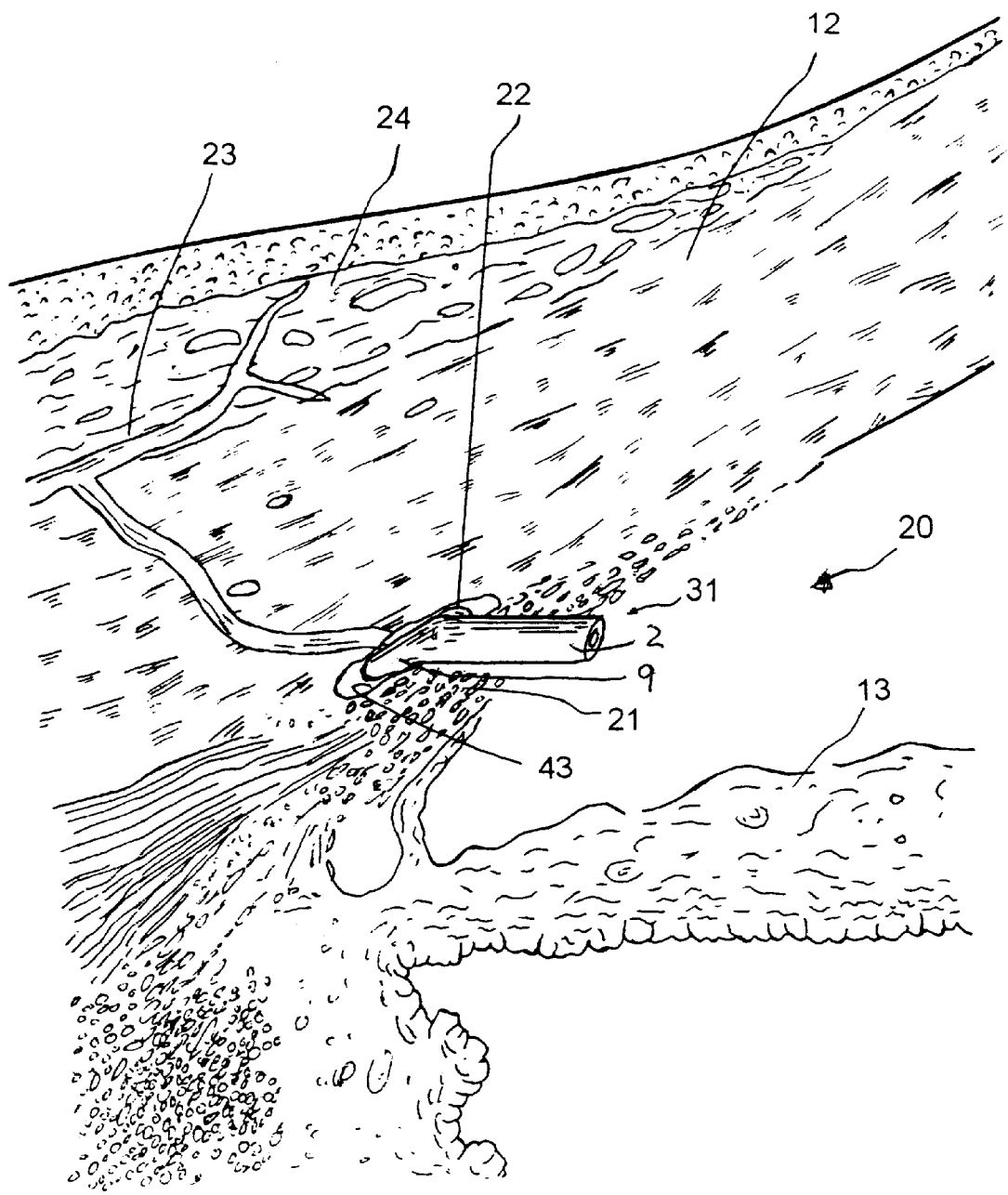
FIG. 8 is a perspective view of the anterior chamber of an eye, illustrating the glaucoma device of the present invention positioned within the trabecular meshwork.

As shown in FIG. 2, the trabecular meshwork 21 is adjacent a small portion of the sclera 11. Traditional procedures that create a hole or opening for implanting a device through the tissues of the conjunctiva 24 and sclera 11 involve extensive surgery, as compared to surgery for implanting a device which ultimately resides entirely within the confines of the sclera 11 and cornea 12, as is performed in accordance with one aspect of the present invention. A device 31 for establishing an outflow pathway, positioned through the trabecular meshwork 21, is illustrated in FIG. 8.

One aspect of the invention includes a method for increasing aqueous humor outflow in an eye of a patient, to reduce the intraocular pressure therein. The method comprises bypassing the trabecular meshwork 21. The device 31 may be elongate or of other appropriate shape, size, or configuration, as will be evident to those of skill in the art. In one embodiment, illustrated in FIG. 3, the device has an inlet section, a middle section 4, and an outlet section 9. There is also at least one lumen inside at least one of the sections for transmitting aqueous humor. The inlet section is typically positioned at an anterior chamber 20 of the eye and the outlet section 9 is preferably positioned at about an exterior surface of the trabecular meshwork 21. The outlet section 9 is, in some embodiments, substantially perpendicular to the middle section 4a. "Substantially perpendicular," as used herein, is defined as subtending an angle between the long axes of the sections (e.g., the outlet section 9 and middle section 4) of between about 30 degrees and about 150 degrees.

The middle section 4A is advantageously placed across the trabecular meshwork 21 through a slit or opening. This opening can be created by laser, a knife, or other surgical cutting instrument. The opening may advantageously be substantially horizontal, i.e., extending longitudinally in the same direction as the circumference of the limbus 15. Other opening directions may also be used, such as horizontal or at any angle that is appropriate for inserting the glaucoma device through the trabecular meshwork 21 and into Schlemm's canal or another outflow pathway, as will be apparent to those of skill in the art. The middle section 4A may be semi-flexible and/or adjustable in position relative to the inlet section 2 and/or outlet section 9, further adapting the device for simple and safe glaucoma implantation. Furthermore, the outlet section 9 may be positioned into fluid collection channels of the natural outflow pathways. Such natural outflow pathways include Schlemm's canal 22, aqueous collector channels, aqueous veins, and episcleral veins. The outlet section 9 may be positioned into fluid collection channels up to at least the level of the aqueous veins, with the device inserted in a retrograde or antegrade fashion.

A further aspect of the invention includes methods for increasing aqueous humor outflow in an eye of a patient to reduce an intraocular pressure therein. The method comprises the following: (a) creating an opening in the trabecular meshwork 21, wherein the trabecular meshwork 21 includes a deep side and superficial side; (b) inserting a glaucoma device into the opening; and (c) transmitting aqueous humor through the device, to bypass the trabecular meshwork 21, from the deep side to the superficial side of the trabecular meshwork 21. This "transmitting" of aqueous humor is, in one aspect of the invention, preferably passive, i.e., aqueous humor is allowed to flow out of the anterior chamber due to the pressure gradient between the anterior chamber and the aqueous venous system.

Figure 3:
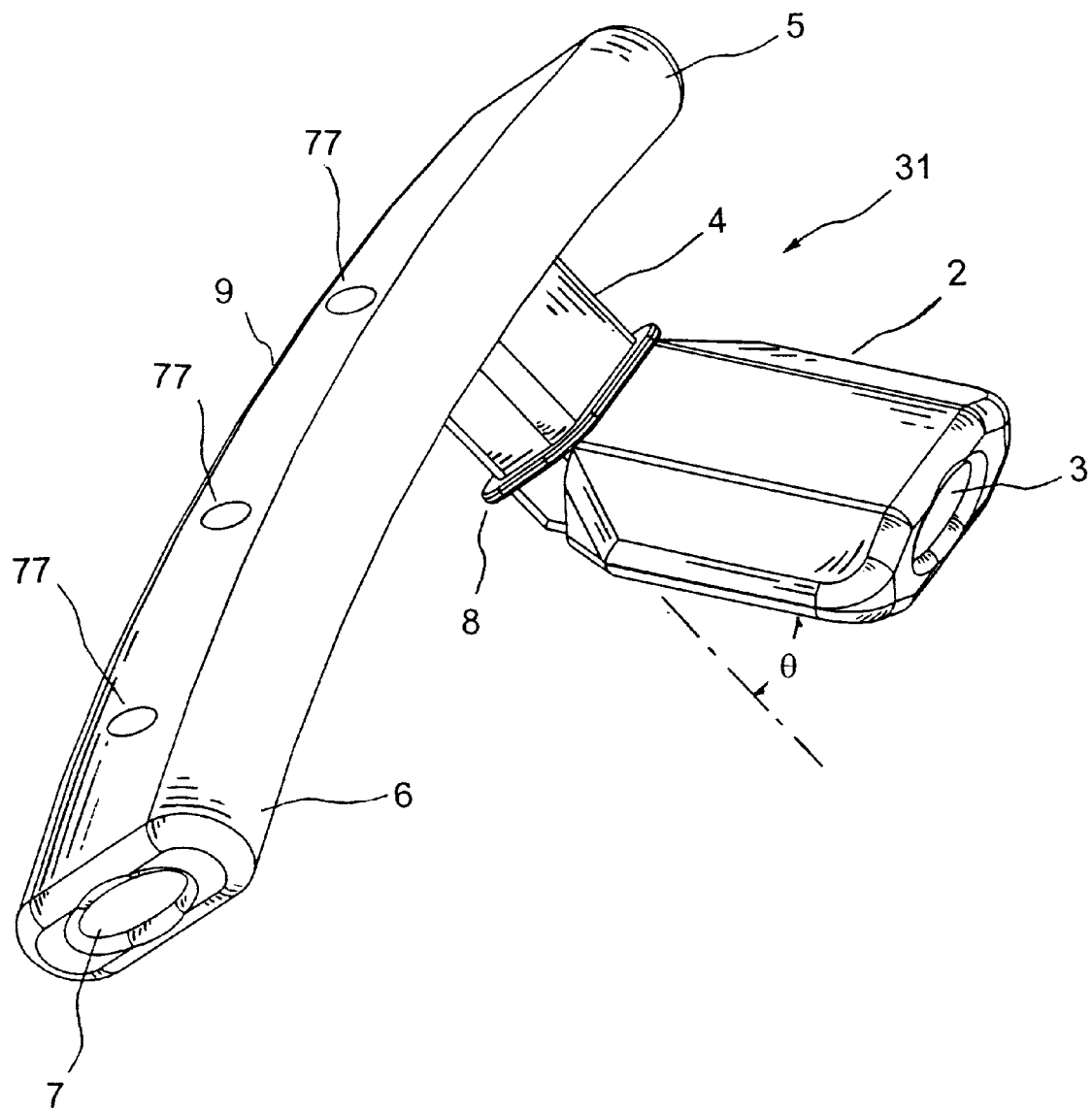
FIG. 3 is an oblique elevational view of a glaucoma device according to the present invention.

FIG. 3 shows an embodiment of the glaucoma device 31 according to the principles of the invention. The device may comprise a biocompatible material, such as medical grade silicone, e.g., Silastic™, available from Dow Corning Corporation of Midland, Mich.; or polyurethane, e.g., Pellethane™, also available from Dow Corning Corporation.

In an alternate embodiment, other biocompatible material (biomaterial) may be used, such as polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilison, mixture of biocompatible materials, and the like. In a further embodiment, a composite biocompatible material may be used, wherein a surface material may be used in addition to one or more of the aforementioned materials. Such a surface material may include polytetrafluoroethylene ("PTFE") (such as Teflon™), polyimide, hydrogel, heparin, therapeutic drugs (such as beta-adrenergic antagonists and other antiglaucoma drugs, or antibiotics), and the like.

The device facilitates the outflow of aqueous from the anterior chamber 20 into Schlemm's canal 22, and subsequently into the aqueous collectors and the aqueous veins so that the intraocular pressure is reduced. In one embodiment, as shown in FIG. 3, the device 31 comprises an inlet section 2, a middle section 4, and an outlet section 9. The middle section 4 may be an extension of, or may be coextensive with, the inner section. The device 31 further comprises at least one lumen within, one, two, or all three sections 2, 4, 9 for transmitting aqueous humor from the inlet opening 3.

In some embodiments, a curved and/or flexible outlet section 9 is positioned inside one of the natural outflow pathways. The outlet section 9 may have a first outlet end 6 and a second, opposite outlet end 5. The outlet section 9 may further have at least one vent or opening 7 at one outlet end of the outlet section 9, and/or a plurality of side openings 77, for transmitting aqueous humor. The middle section 4 is connected to or coextensive with the outlet section 9 between the first outlet end 6 and the second outlet end 5. In a preferred arrangement, the outlet section 9 is curved around a point, or curve center, and the middle section extends substantially along a plane that contains the curve center. In one embodiment, the radius of the curve of the outlet section 9 is between about 4 mm and about 10 mm.

The device is preferably biocompatible so that any inflammation caused by irritation between the outer surface of the device and surrounding tissue is minimal. All or a portion of the cross-section of one or more lumens may be in an elliptical (e.g., oval) shape. Furthermore, the outlet section inside the outflow pathway may have an appropriate shape, e.g., with a protuberance or barb projecting from it, to stabilize the device in place without undue suturing.

In some embodiments, the radius of the curve of the outlet section 9 is between about 4 mm and 10 mm.

An optional ridge or flange 8 at the junction of the inlet section 2 and the middle section 4 may be provided for device stabilization purposes. The appropriate length of the middle section 2 that is adjacent to the ridge 8 and the outlet section 9 is, in one embodiment, preferably close in thickness to the trabecular meshwork 21, which is approximately between about 100 microns and about 300 microns thick.

The shape of the opening 7 of the outlet section 6 and the remaining body of the outlet section 9 may be oval, round, or other appropriate shape. The shape in some embodiments preferably conforms to the shape of the outflow pathway into which the outlet section 9 is placed. The opening 7 of the outlet end may be ovoid in shape to match the contour of Schlemm's canal 22. Further, an outer contour of the outlet section 9 may be elliptical (e.g., ovoid) in shape to match the contour of Schlemm's canal 22. This minimizes rotational movement of the outlet section 6 within Schlemm's canal 22, and thereby stabilizes the inlet section 2 with respect to the iris and cornea.

Figure 4:
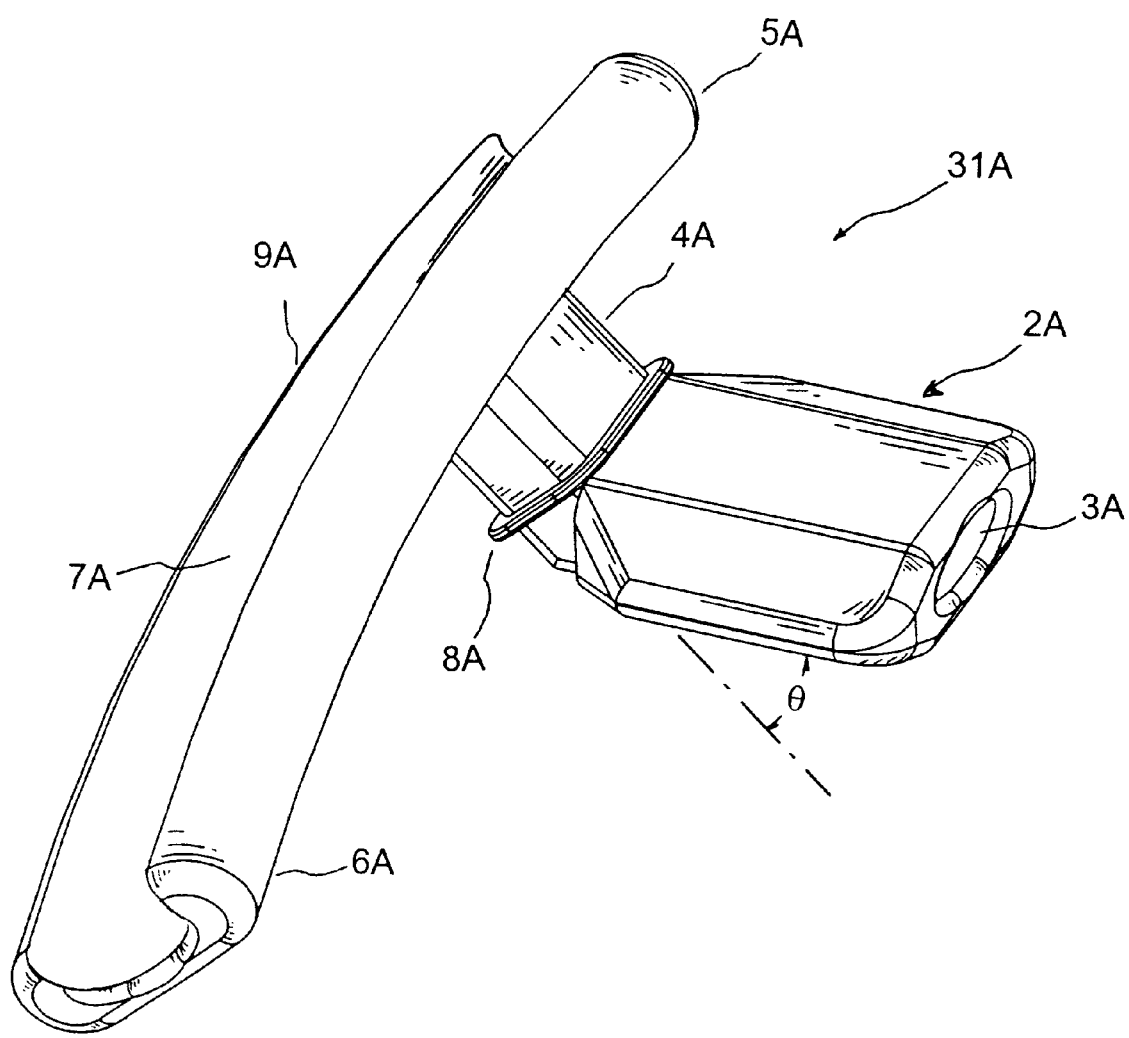
FIG. 4 is an oblique elevational view of the glaucoma device, featuring an open trough configuration.

FIG. 4 shows another embodiment of the glaucoma device according to principles of the present invention. The device 31A comprises an inlet section 2A, a middle section 4A, and an outlet section 9A. The device further comprises at least one lumen inside the glaucoma device 31A throughout one or more of the three sections 2A, 4A, 9A for transmitting aqueous humor starting from the inlet opening 3A. A curved and/or flexible outlet section 9A is used for positioning the outlet section 9A inside one of the existing outflow pathways. The outlet section 9A may comprise an elongated trough 7A or groove for transmitting, or venting, aqueous humor. The elongated trough is connected to and in communication with the at least one lumen inside the glaucoma device as shown in FIG. 4. An optional ridge 8A at the junction of the inlet section 2A and the middle section 4A is provided for stabilization purposes.

As shown in FIGS. 3 and 4, the device of the present invention may have a length between about 0.5 mm to over ten centimeters, depending on the distance between the anterior chamber and drainage vessel (e.g., a vein) into which the device drains aqueous humor. The outside diameter of the device may range from about 30 μm to about 500 μm. The diameter of the device lumen is advantageously in the range of about 20 μm to about 250 μm. The device may have a plurality of lumens to facilitate transmission of multiple flows of aqueous humor. The long axis of the inlet section 2, 2A may be at an angle (θ) between about 20 degrees and about 150 degrees, preferably between about 30 and about 60 degrees, with respect to the long axis of the middle section 4, 4A.

The glaucoma device of the present invention, which may also be called a trabecular shunt, may be made by molding, thermo-forming, or other micro-machining techniques. Biomaterial suitable for the manufacturing the device may include polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilison, and/or a mixture of the above biocompatible materials.

Figure 5A:
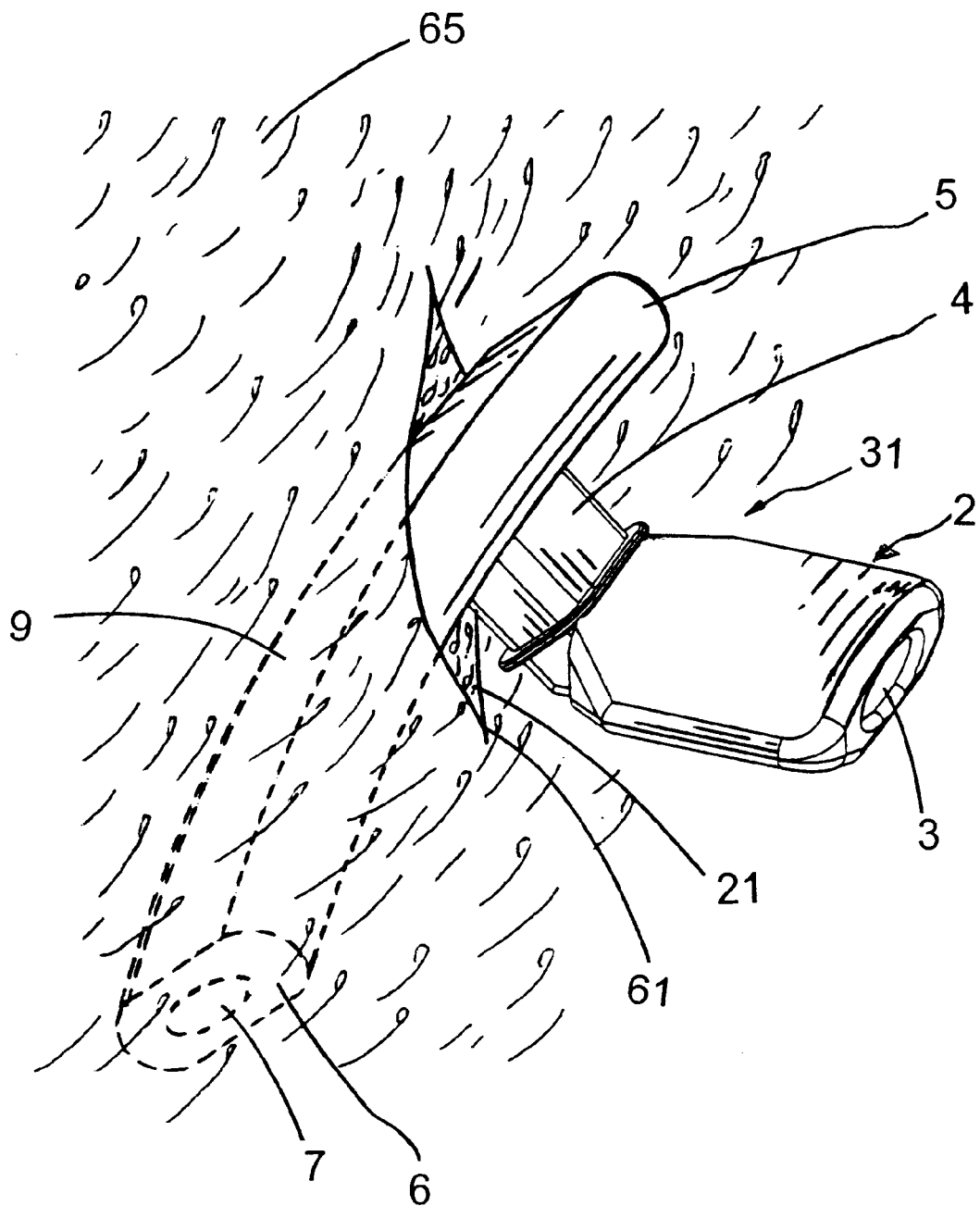
FIG. 5A illustrates placement of one end of the glaucoma device through trabecular meshwork in accordance with the present invention.
Figure 6:
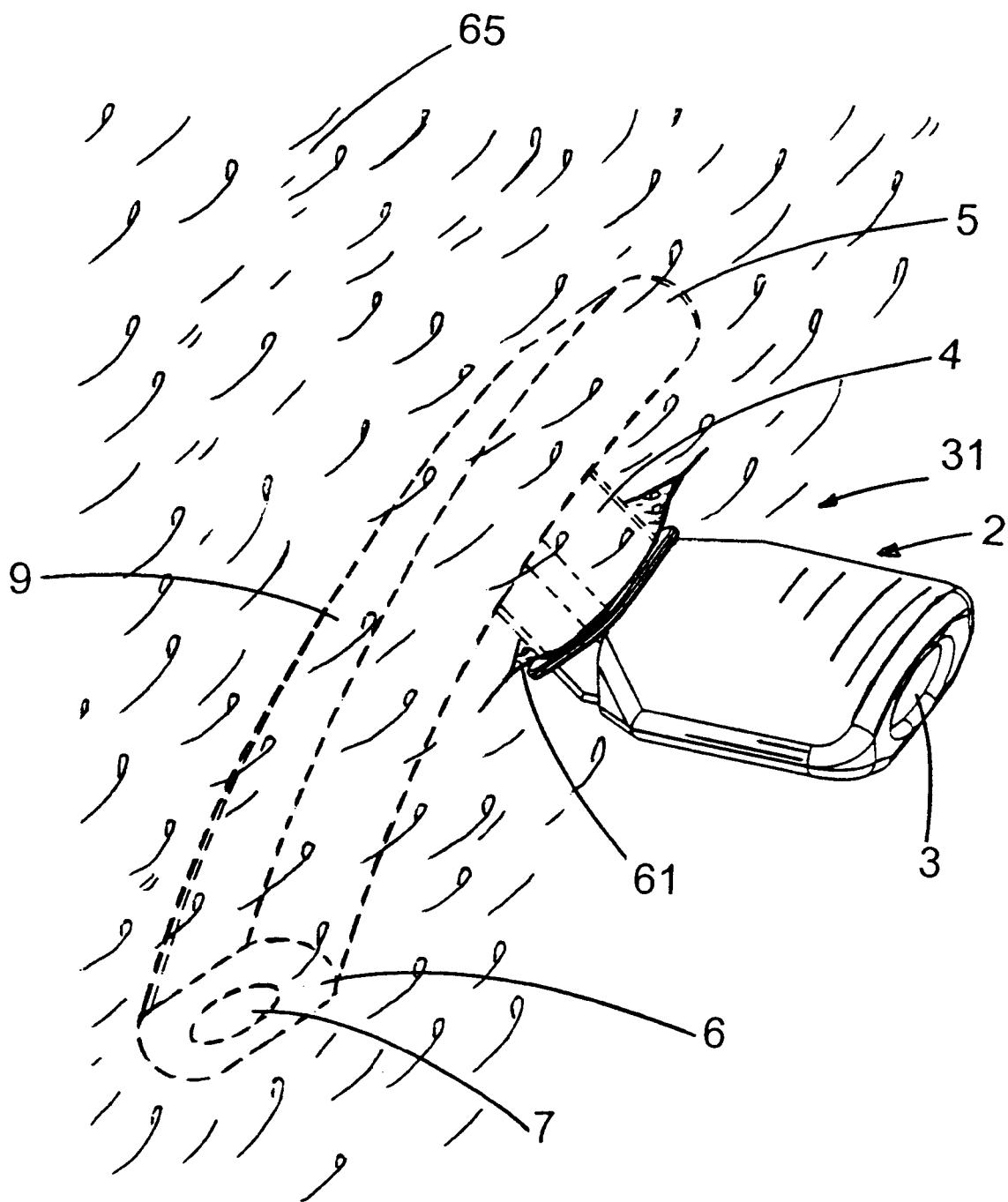
FIG. 6 illustrates completed placement of the glaucoma device through trabecular meshwork.

FIG. 5A illustrates a step in deploying the glaucoma device through the trabecular meshwork 21. The outlet section 9 of the device 31 is, in one aspect of the invention, inserted into an opening 61 in the trabecular meshwork 21. The slit or opening 61 may be created ab interno from the interior surface 65 of the trabecular meshwork 21. The surgeon then advances the first outlet end 6 of the outlet section 9 through the opening 61 into a first side of Schlemm's canal or other suitable outflow pathway. The surgeon then advances the second outlet end 5 of the outlet section 9 through the opening 61 and into a second side of Schlemm's canal. This may be facilitated by slightly pushing the second outlet end 5 through the opening 61. FIG. 6 illustrates a further stage in deployment of the device, wherein the whole outlet section 9 of the device 31 is inside the outflow pathway (e.g., Schlemm's canal), beneath the trabecular meshwork 21. An enhanced fluid communication through the trabecular meshwork 21 at this stage is through the lumen of the implanted device 31.

Figure 5B:
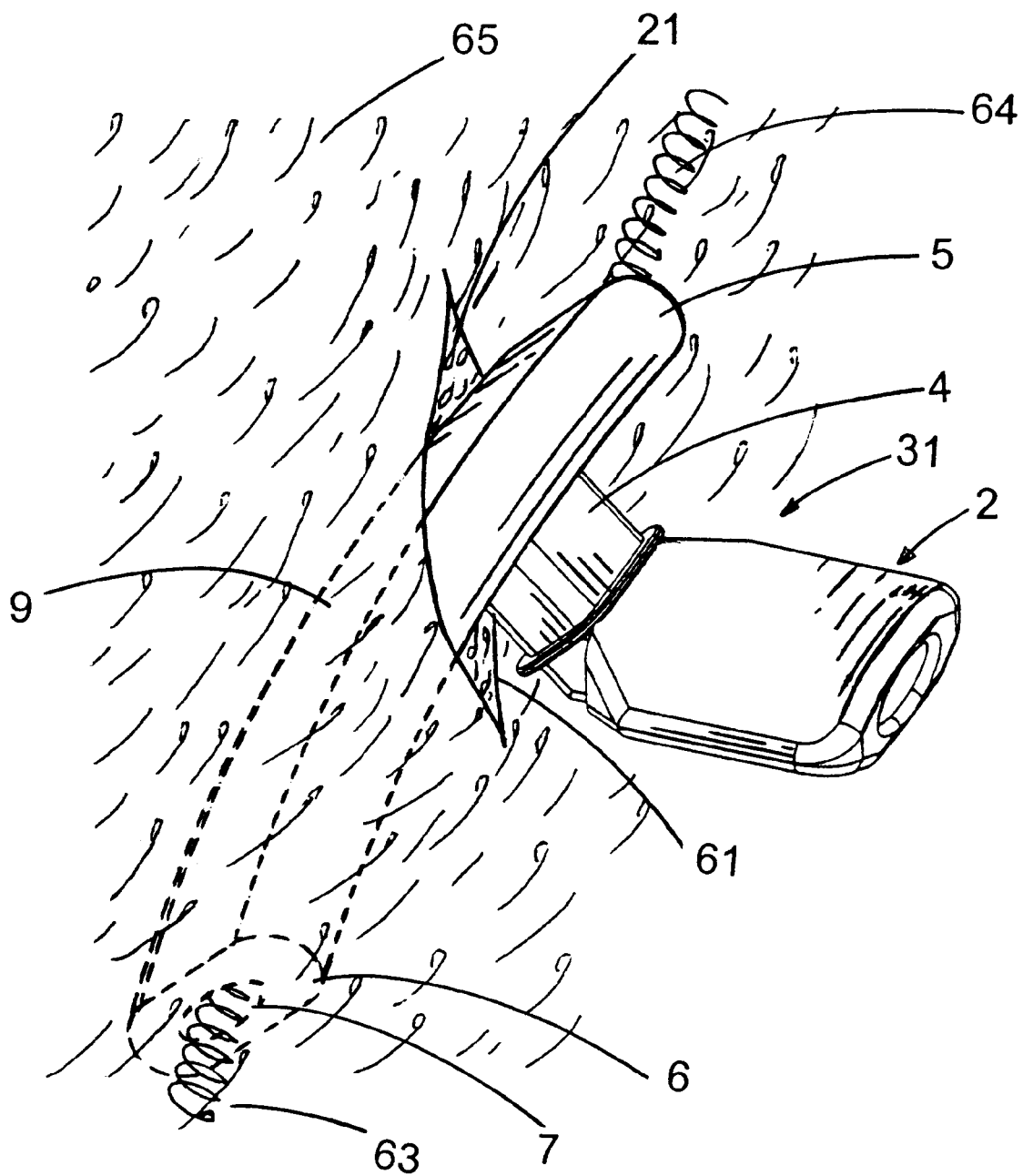
FIG. 5B illustrates an alternate method of placement of one end of the glaucoma device through trabecular meshwork, over a guidewire.

FIG. 5B, shows an additional and/or alternate step of deploying the glaucoma device. The surgeon can insert a distal end 63 of a guidewire 64 through the opening 61 into the first side Schlemm's canal, or other outflow pathway, to guide the device 31 into position during the device implantation. The step of advancing the first outlet end 6 of the outlet section 9 into Schlemm's canal is accomplished, in this embodiment, by "riding," or advancing, the glaucoma device 31 on the guidewire 64. A cross-section of the guidewire may advantageously be selected from any of the following: an elliptical (e.g., oval) shape, D-shape, round shape, and irregular (asymmetric) shape adapted for nonrotatory engagement for the device.

Figure 7:
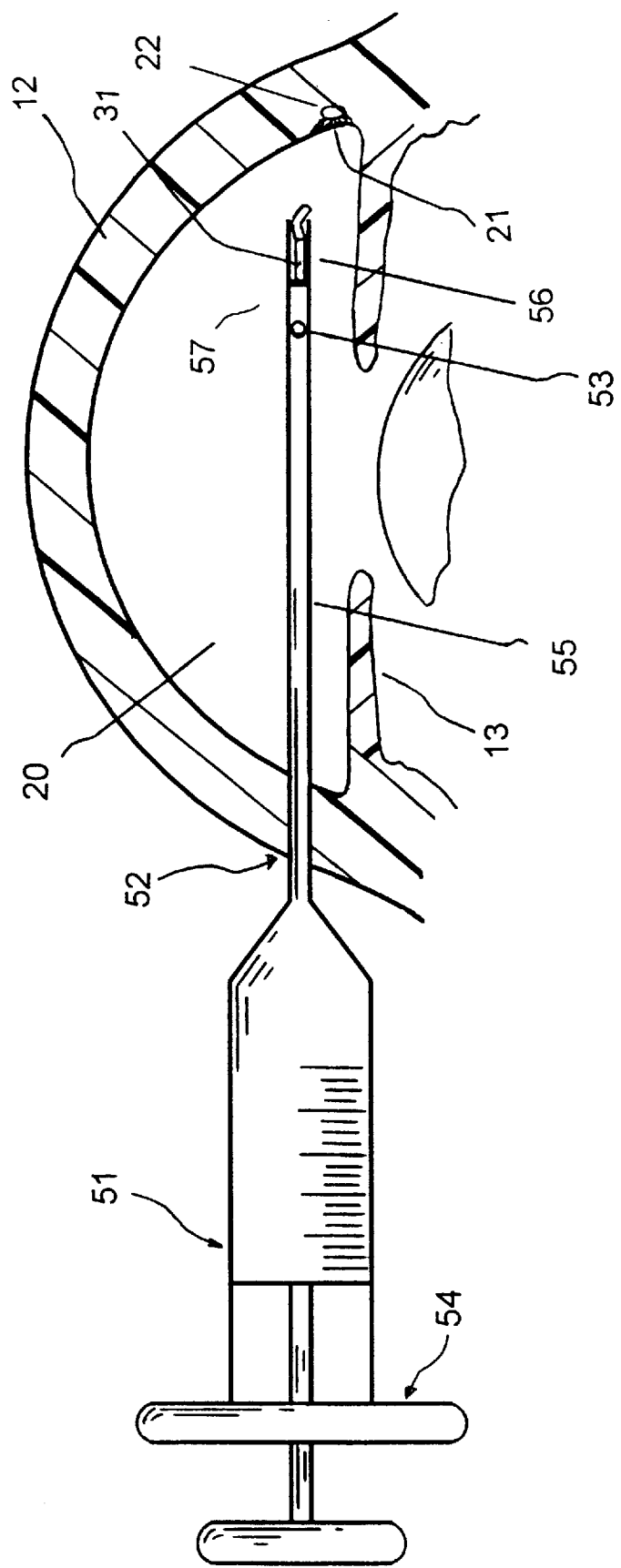
FIG. 7 illustrates a method of placement of the glaucoma device in an eye in accordance with the present invention.

FIG. 7 shows an aspect of placing the glaucoma device at the implantation site. An irrigating knife or applicator 51 is provided, which, in some embodiments, comprises a syringe portion 54 and a cannula portion 55. The distal section of the cannula portion 55 has at least one irrigating hole 53 and a distal space 56 for holding the device 31. The proximal end 57 of the lumen of the distal space 56 is, in one embodiment, sealed off from, and thus substantially not in communication with, the remaining lumen of the cannula portion 55. In this embodiment, the device is placed on the delivery applicator and advanced to the device site, wherein the delivery applicator holds the device securely during delivery and releases it when the surgeon chooses to deploy the device.

In some embodiments of trabecular meshwork surgery in accordance with the invention, the patient is placed in the supine position, prepped, draped, and anesthetized as necessary. In one embodiment, a small (less than 1-mm incision, which may be self-sealing, is made through the cornea. Through this incision, the trabecular meshwork 21 is accessed, and an incision is made in the trabecular meshwork 21 with an irrigating knife. The device 31 is then advanced through the corneal incision 52 across the anterior chamber 20, while the device is held in an irrigating applicator 51, under gonioscopic, microscopic, or endoscopic guidance. After the device is implanted in place, the applicator is withdrawn and the surgery concluded. The irrigating knife may be within a size range of about 16 to about 40 gauge, and, in some embodiments, preferably about 30 gauge.

FIG. 8 illustrates the device 31 positioned within the tissue of an eye 10. An opening is present in the trabecular meshwork 21. The outlet section 9 of the device 31 has been inserted into the opening. The inlet section 2 is exposed to the anterior chamber 20, while the outlet section 9 is positioned near an interior surface 43 of the trabecular meshwork 21. In a further embodiment, the outlet section 9 may further be placed into fluid collection channels, as described above. A device as shown in FIG. 4, wherein the outflow section has an open trough for stenting purposes, may be used to maintain the opening of one or more of these outflow pathways, In one embodiment, the method of forming an opening in the trabecular meshwork 21 may comprise making an incision with a microknife, a pointed guidewire, a sharpened applicator, a screw-shaped applicator, an irrigating applicator, or a barbed applicator. Alternatively, the trabecular meshwork 21 may be dissected with an instrument similar to a retinal pick or microcurrette. The opening may alternately be created by fiberoptic laser ablation.

Figure 9:
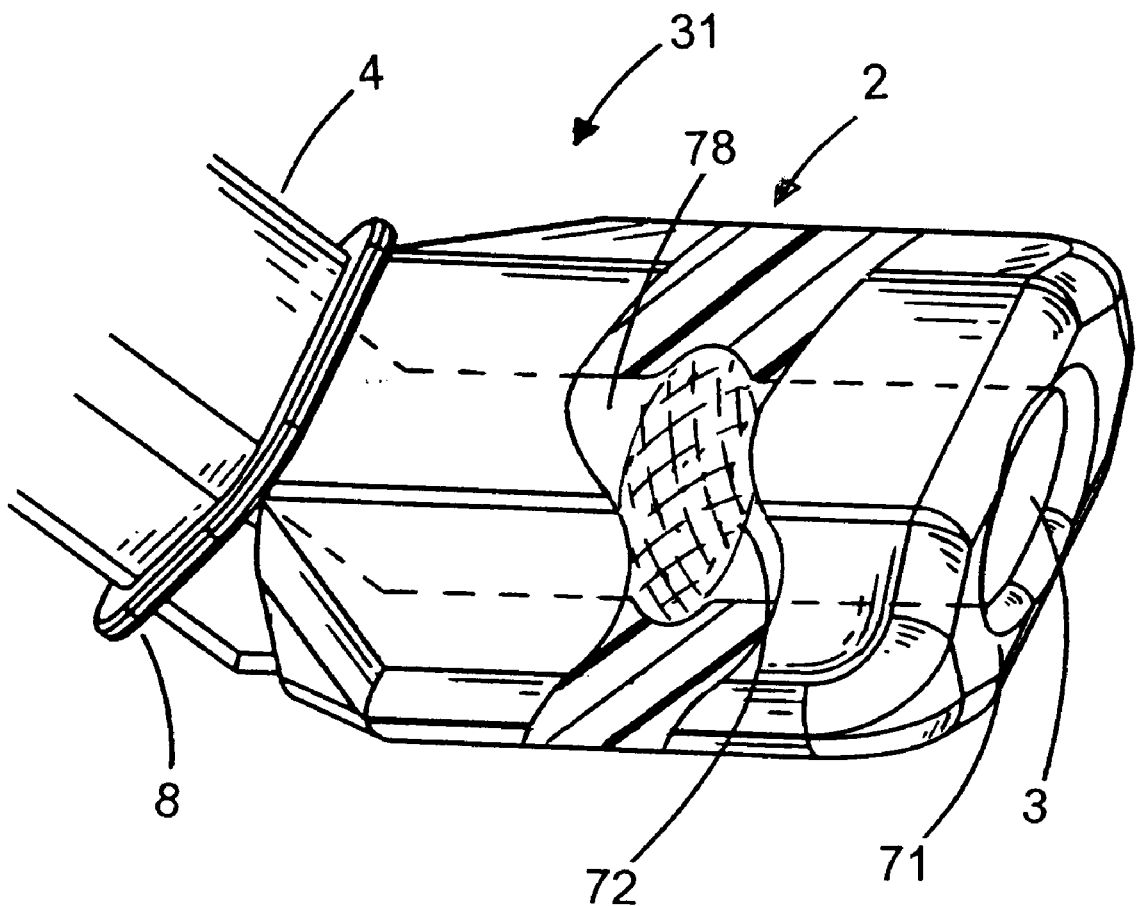
FIG. 9 is a close-up view of the inlet section of the glaucoma device in accordance with the present invention., illustrating a flow-restricting member inside the lumen of the inlet section.

FIG. 9 is a close-up view of the inlet section 2 of the glaucoma device 31, having a flow-restricting member 72 inside a lumen 78 of the glaucoma device. The flow-restricting member 72 is shown located close to the inlet side 71 of the inlet section 2. Alternatively, the flow-restricting member may be situated in any location in the device that will cause the flow of blood to be restricted from moving retrograde, i.e., from the outlet section 9 to the anterior chamber 20 of the eye. The flow-restricting member is used to selectively restrict at least one component in blood from backflowing into the anterior chamber 20. The flow-restricting member may, in some embodiments, be a filter made of a type of material selected from the following filter materials: expanded polytetrafluoroethylene, cellulose, ceramic, glass, Nylon, plastic, and fluorinated material such as polyvinylidene fluoride ("PVDF") (trade name: Kynar, by DuPont). Advantageously, the flow-restricting member 72 tightly occupies a section of the flow lumen 78 of the at least one lumen between the inlet section 2 and the outlet section 9.

From the foregoing description, it will be appreciated that a novel approach for the surgical treatment of glaucoma has been disclosed. While aspects of the invention have been described with reference to specific embodiments, the description is illustrative and is not intended to limit the scope of the invention. Various modifications and applications of the invention may occur to those who are skilled in the art, without departing from the true spirit or scope of the invention. The breadth and scope of the invention should be defined only in accordance with the appended claims and their equivalents.

What is claimed is:

1. A method of placing a glaucoma device into an opening through trabecular meshwork and into an outflow pathway for aqueous humor, said glaucoma device comprising an inlet section, an outlet section, a middle section between the inlet section and the outlet section, and at least one lumen that extends within at least one of said sections for transmitting aqueous humor, wherein the outlet section is substantially perpendicular to the middle section, and wherein the outlet section comprises a first outlet end and a second outlet end; the method comprising:

advancing the first outlet end of the outlet section through said opening into a first part of the outflow pathway; and advancing the second outlet end of the outlet section through said opening into a second part of the outflow pathway; and inserting a guidewire through said opening into the first part of the outflow pathway, wherein said advancing the first outlet end of the outlet section comprises advancing said glaucoma device along said guidewire.

2. A method of placing a glaucoma device into an opening through trabecular meshwork and into an outflow pathway for aqueous humor, said glaucoma device comprising an inlet section, and outlet section, a middle section between the inlet section and the outlet section, and at least one lumen that extends within at least one of said sections for transmitting aqueous humor, wherein the outlet section is substantially perpendicular to the middle section, and wherein the outlet section comprises a first outlet end and a second outlet end; the method comprising:

advancing the first outlet end of the outlet section through said opening into a first part of the outflow pathway;

advancing the second outlet end of the outlet section through said opening into a second part of the outflow pathway; and inserting a guidewire through said opening into the first part of the outflow pathway, wherein said advancing the first outlet end of the outlet section comprises advancing said glaucoma device along said guidewire;

wherein a cross-sectional shape of said guidewire is selected from the group consisting of elliptical, D-shaped, round, and irregularly shaped.

* * * * *

UNITED STATES PATENT AND TRADEMARK OFFICE
CERTIFICATE OF CORRECTION

PATENT NO. : 6,736,791 B1  
DATED : May 18, 2004  
INVENTOR(S) : Hosheng Tu, Olav B. Bergheim and Morteza Gharib Page 1 of 1

It is certified that error appears in the above-identified patent and that said Letters Patent is hereby corrected as shown below:

<u>Title page,</u>  
Item [75], Inventors, should read as follows:  
-- Hosheng Tu, Tustin, CA (US); Olav B. Bergheim, Laguna Hills, CA (US); Morteza Gharib, San Marino, CA (US) --

Signed and Sealed this

Eleventh Day of January, 2005

JON W. DUDAS  
*Director of the United States Patent and Trademark Office*

UNITED STATES PATENT AND TRADEMARK OFFICE
CERTIFICATE OF CORRECTION

PATENT NO. : 6,736,791 B1
DATED : May 18, 2004
INVENTOR(S) : Hosheng Tu, Olav B. Bergheim and Morteza Gharib It is certified that error appears in the above-identified patent and that said Letters Patent is hereby corrected as shown below:

Column 12,
Line 5, please delete "pathway; and" and insert therefore, -- pathway; --.
Line 17, please delete "section, and outlet" and insert therefore, -- section, an outlet --.

Signed and Sealed this

Thirty-first Day of May, 2005

JON W. DUDAS
*Director of the United States Patent and Trademark Office*